US010123901B2

United States Patent
Frantz et al.

(10) Patent No.: US 10,123,901 B2
(45) Date of Patent: Nov. 13, 2018

(54) METHOD AND APPARATUS FOR VACUUM-FORMED DENTAL APPLIANCE

(71) Applicant: Frantz Design Incorporated, Austin, TX (US)

(72) Inventors: Joseph Lee Frantz, Austin, TX (US); Donald Frantz, Katy, TX (US)

(73) Assignee: Frantz Design Incorporated, Austin, TX (US)

( * ) Notice: Subject to any disclaimer, the term of this patent is extended or adjusted under 35 U.S.C. 154(b) by 847 days.

(21) Appl. No.: 14/478,511

(22) Filed: Sep. 5, 2014

(65) Prior Publication Data

US 2015/0059766 A1     Mar. 5, 2015

Related U.S. Application Data

(63) Continuation of application No. 13/520,520, filed as application No. PCT/US2011/030367 on Mar. 29, 2011, now Pat. No. 8,882,497.

(Continued)

(51) Int. Cl.
*A61F 5/56*     (2006.01)

(52) U.S. Cl.
CPC ..................... *A61F 5/566* (2013.01)

(58) Field of Classification Search
CPC .... A61F 5/566; A61F 5/58; A61F 5/56; A61F 2005/563; A61C 7/08; A61C 19/063; A61B 5/4547; A61B 5/4552; A61B 5/4557; A61B 5/682; A61B 5/0534; A63B 71/085; A63B 2071/086; A63B 2017/088
See application file for complete search history.

(56) References Cited

U.S. PATENT DOCUMENTS

| 5,947,724 | A |   | 9/1999 | Frantz |
| 6,109,265 | A | * | 8/2000 | Frantz ..................... A61F 5/566 |
|           |   |   |        | 128/848 |

(Continued)

FOREIGN PATENT DOCUMENTS

| JP | 2009028084 | 2/2009 |
| WO | 2008048649 | 4/2008 |
| WO | 2009155223 | 12/2009 |

OTHER PUBLICATIONS

PCT Written Opinion of the International Searching Authority PCT/US2011/030367 dated Nov. 11, 2011.

*Primary Examiner* — Tarla Patel
(74) *Attorney, Agent, or Firm* — Invention Mine LLC

(57) ABSTRACT

An appliance and methods are described that include embodiments of a mandibular advancement or positioning device which can use elastic bands to pull the jaw forward. The appliance has an upper plastic tray conforming to the patient's upper teeth and including a set of retention hooks coupled to the upper plastic tray via being encased in plastic, one on the right and one on the left anterior buccal portion of an upper plastic base. The appliance also has a lower plastic tray conforming to the patient's lower teeth and has a set of bite pads integrated with a second set of plastic retention hooks encased in plastic extending outwardly from the teeth. The appliance includes the upper and lower plastic trays and specially formed elastic bands of a plurality of lengths and strengths replaceably attached to the retention hooks on both sides of the trays to pull the mandible forward for treatment.

5 Claims, 6 Drawing Sheets

Related U.S. Application Data

(60) Provisional application No. 61/318,662, filed on Mar. 29, 2010.

(56) References Cited

U.S. PATENT DOCUMENTS

| | | | |
|---|---|---|---|
| 7,637,262 B2 * | 12/2009 | Bailey | A61F 5/566 128/848 |
| 2007/0283967 A1 | 12/2007 | Bailey | |
| 2009/0032030 A1 * | 2/2009 | Callender | A61F 5/566 128/845 |
| 2009/0036889 A1 * | 2/2009 | Callender | A61F 5/566 606/55 |
| 2013/0095446 A1 | 4/2013 | Andreiko | |
| 2015/0007830 A1 | 1/2015 | Remmers | |

* cited by examiner

METHOD AND APPARATUS FOR VACUUM-FORMED DENTAL APPLIANCE

CROSS REFERENCE

The present application is a continuation of U.S. patent application Ser. No. 13/520,520, now U.S. Pat. No. 8,882,497, titled "METHOD AND APPARATUS FOR VACUUM-FORMED DENTAL APPLIANCE", filed Jul. 3, 2012, which is a national stage application under 35 U.S.C. 371 of International Application PCT/US2011/030367, titled "METHOD AND APPARATUS FOR VACUUM-FORMED DENTAL APPLIANCE", filed on Mar. 29, 2011, which claims benefit under 35 U.S.C. § 119(e) to U.S. provisional application 61/318,662, titled "METHOD AND APPARATUS FOR VACUUM-FORMED DENTAL APPLIANCE" filed Mar. 29, 2010.

FIELD

This invention relates generally to oral appliances for preventing or at least alleviating snoring and sleep apnea. At the present, there is no known vacuum formed, non-invasive, inexpensive custom dentist-made sleep disorder breathing appliance. Known trial sleep apnea appliances have been made of bulky boil & bite materials. More specifically, this invention relates to a dental office manufacturing method utilizing techniques and machines in most dental offices to manufacture a trial removable mandibular advancement appliance which can use elastic bands to pull the jaw forward and bite pads to open the bite vertically. In addition to the foregoing, other method aspects are described in the claims, drawings, and text forming a part of the present disclosure.

SUMMARY

An appliance and methods are described that include embodiments of a mandibular advancement or positioning device which can use elastic bands to pull the jaw forward. The appliance has an upper plastic tray conforming to the patient's upper teeth and including a set of retention hooks coupled to the upper plastic tray via being encased in plastic, one on the right and one on the left anterior buccal portion of an upper plastic base. The appliance also has a lower plastic tray conforming to the patient's lower teeth and has a set of bite pads integrated with a second set of plastic retention hooks encased in plastic extending outwardly from the teeth. The appliance includes the upper and lower plastic trays and specially formed elastic bands of a plurality of lengths and strengths replaceably attached to the retention hooks on both sides of the trays to pull the mandible forward for treatment. An embodiment provides a method of making a trial dental appliance for a patient including temporarily attaching a first set of retention hooks to models of the patient's upper teeth; temporarily attaching a set of bite pads integrated with a second set of retention hooks to the model of the patient's lower teeth; vacuum forming sheets of plastic over the models of the patent's upper and lower teeth with the temporarily attached first set of retention hooks and the set of bite pads integrated with the second set of retention hooks in a machine to form upper and lower plastic trays vacuum-formed to fit over the teeth of the patient, the heat from the vacuum machine enabling the sheets of plastic to encase the temporarily attached first set of retention hooks and the set of bite pads integrated with the second set of retention hooks; and removing the trays from the models with the incased parts, the removal of the trays detaching the first set of retention hooks and the set of bite pads integrated with the second set of retention hooks from the models to form the dental appliance to enable attachment of a pair of elastic bands to be placed over the first and second sets of encased retention hooks. In addition to the foregoing, other system aspects are described in the claims, drawings, and text forming a part of the present disclosure.

An embodiment provides an oral appliance including upper and lower trays adapted to fit tightly but removably over the occlusal surfaces of the upper and lower teeth of a patient; a first set of retention hooks encased by the upper tray; a set of bite pads integrated with a second set of retention hooks encased by the lower tray to form a bite plane on the occlusal surface of both sides of the lower tray, each bite pad having a bite surface which protrudes therefrom so as to engage the occlusal surfaces on the upper tray and thus maintain the occlusal surfaces of the trays in predetermined spaced relation, when the trays are so fitted; and means to releasably attach the anterior and posterior portions of both sides of each tray using the first set of retention hooks and the second set of retention hooks to enable a lower jaw to advance forwardly when the upper and lower trays are fitted over the patient's teeth. In addition to the foregoing, other computer program product aspects are described in the claims, drawings, and text forming a part of the present disclosure.

The foregoing is a summary and thus contains, by necessity, simplifications, generalizations and omissions of detail; consequently, those skilled in the art will appreciate that the summary is illustrative only and is not intended to be in any way limiting. Other aspects, features, and advantages of the devices and/or processes described herein, as defined by the claims, will become apparent in the detailed description set forth herein.

BACKGROUND

It is well documented in the literature that an oral appliance that opens the bite and moves the mandible forward will greatly reduce sleep apnea and snoring. It is also documented that these appliances are capable of producing considerable discomfort to patients, unwanted movement of their teeth, and/or temporomandibular joint pain as well as other problems.

A variety of trial oral appliances are available for preventing snoring and sleep apnea. Of these, all are removable, and most advance the mandible, but, to our knowledge, none use elastic bands to move the mandible forward. Heretofore all trial dental sleep appliances have been made of bulky "boil & bite" material. These appliances have not been effective and have not had patient acceptance or compliance. These uncomfortable devices have driven patients away from wanting to be treated by a custom oral appliance.

Also, several removable, oral snoring/apnea appliances are adjustable, pulling the jaw forward in different, set percentages of their maximum movement. However, no existing appliance known to us is totally adjustable, both in amount of forward movement and vertical opening. Instead, temporary or permanent adjustments to appliances are made by either placing spacers, turning screws, or by grinding away plastic or other material. These modifications change the amount of advancement; however, have locked the patient's jaw in one ridged spot causing TMJ pain. Once modifications are made, however, they are permanent until further modified by the doctor. In summary, appliances exist in which the amount of advancement may be changed, but the changes result in a new fixed position of the mandible many times creating pain and discomfort. Other appliances do not offer easily changed vertical or caudal displacement of the mandible to increase the effectiveness of the appliance.

What is needed is a totally adjustable trial oral snoring/sleep apnea appliance which is effective, which has high patient acceptance, and which will not cause temporomandibular joint problems, unwanted tooth movement or soreness. This need is satisfied by the present invention.

The appliance of the present invention is to greatly reduce, or eliminate, sleep apnea and snoring, while alleviating temporomandibular joint problems, unwanted tooth movement and soreness, with complete adjustability of the appliance both in the amount of forward movement of the lower jaw, and in the amount of vertical bite opening. Another object is a mandibular advancement appliance with high patient acceptance, comfort, and treatment success. Another object is to make the appliance in a single office visit using machines normally supplied in a typical dentist's office.

BRIEF DESCRIPTION OF THE DRAWINGS

A better understanding of the subject matter of the application can be obtained when the following detailed description of the disclosed embodiment is considered in conjunction with the following drawing, in which.

The use of the same symbols in different drawings typically indicates similar or identical items.

DETAILED DESCRIPTION

Embodiments herein relate to methods and systems for manufacturing an oral appliance that requires only a single office visit.

During the office visit, a patient can befitted for an oral appliance by first obtaining an upper (maxillary) and lower (mandibular) impression of the teeth and supporting soft tissue including the upper hard palate. This impression must be extremely accurate to avoid tooth soreness, and/or movement when the appliance is placed in the patient's mouth. The impression is taken by: (1) having the patient rinse with a pre-impression mouth wash to eliminate any saliva distortion; and (2) pouring the impressions immediately to avoid distortion using a hard lab stone.

Figure 1:
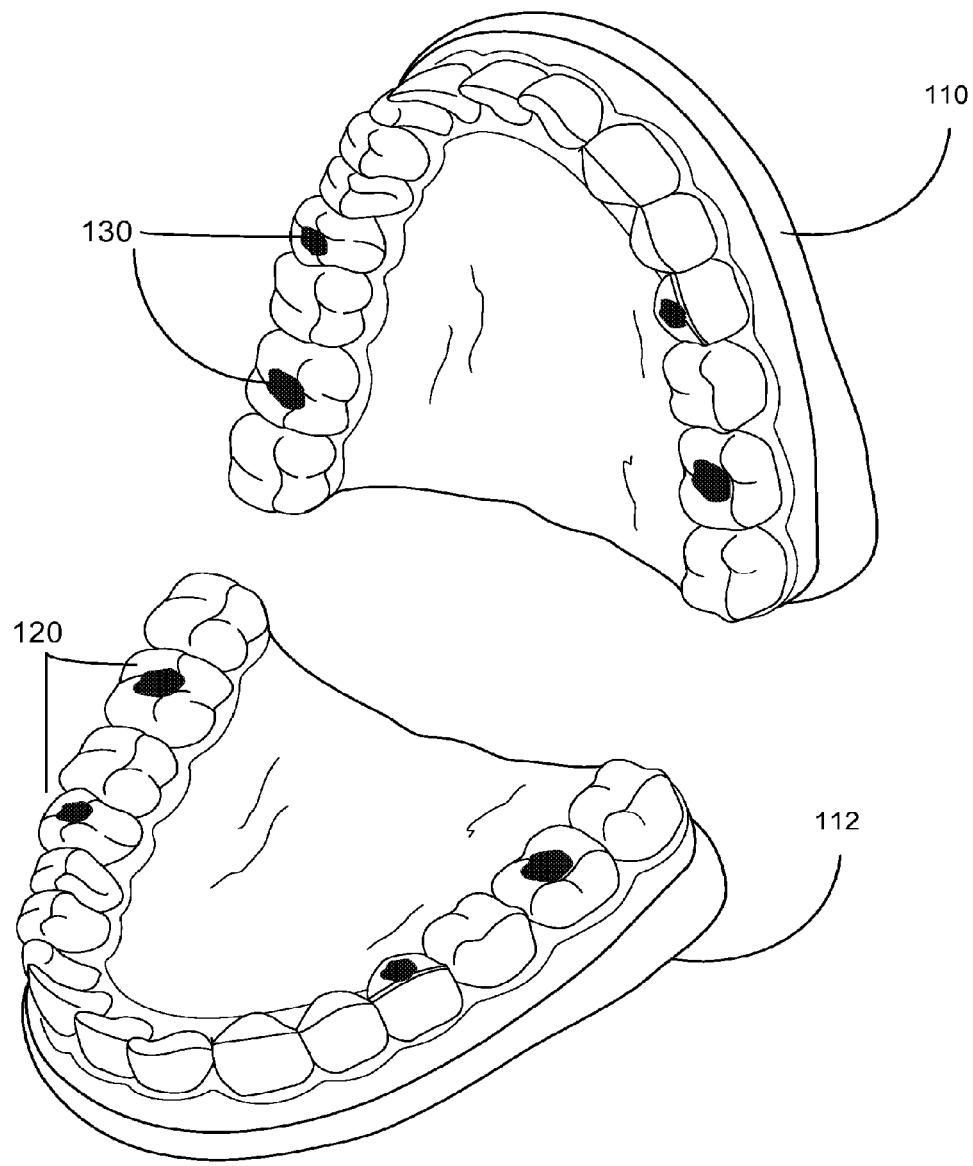
FIG. 1 illustrates a dental mold in accordance with an embodiment of the subject matter of the present application.

Referring now to FIG. 1, the impressions are used to make a model of the patient's teeth 110 and 112. The model 110 and 112 are then altered by temporarily attaching a first set of retention hooks to the model of the patient's upper teeth. The attachment can be by dental wax, glue, such as a polymer glue or Super Glue.

The retention hooks are placed between the cuspid and first bicuspid on the upper model. Next, with the upper models held in centric occlusion with the lower model, a measuring device can be placed over the upper retention hook and with a fine point "Sharpie"™ pen to scribe a mark on the lower model 23, 25, or 27 mm depending on the size of the patient's dental arch. Referring to FIG. 1, marks 120 and 130 illustrate possible locations for marking models 110 and 112. In one embodiment, a kit including an appropriate measuring device can be included to enable proper placement of the marks.

Figure 2:
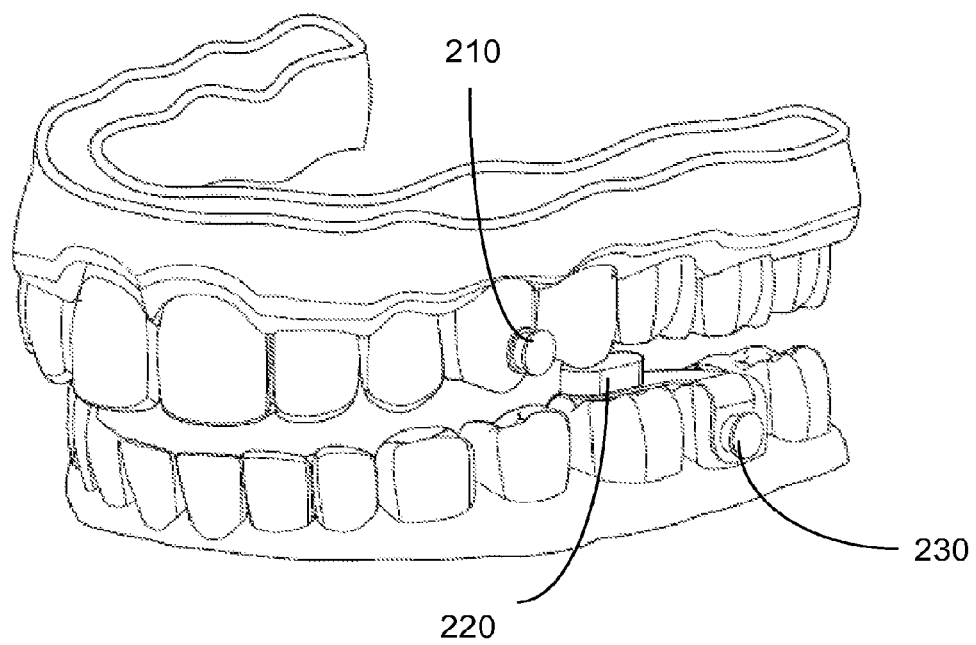
FIG. 2 illustrates a dental mold with bite pads temporarily attached thereon in accordance with an embodiment of the subject matter of the present application. embodiment of the subject matter of the present application.

Referring to FIG. 2, in one embodiment, lower bite pads 220 are temporarily attached. The lower bite pads 220 can be integrated with a second set of retention hooks 230. A scribed line on the lower model in one embodiment can be under the center of the second set of retention hooks and the top portion of the bite pad and should be level with the bite pad on the opposite side of an arch.

Figure 3:
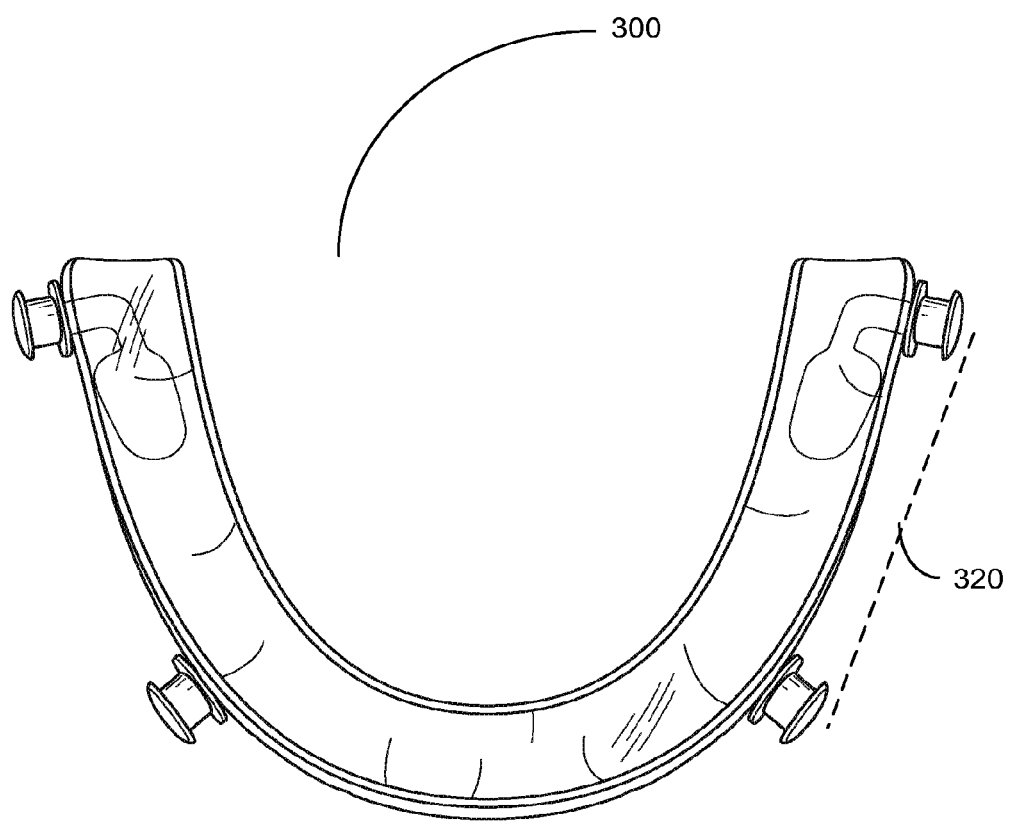
FIG. 3 illustrates a top view of a dental appliance in accordance with an embodiment of the subject matter of the present application.

In one embodiment, the displacement between the corresponding retention hook of the second set of retention hooks and the corresponding retention hook of the first set of retention hooks can be 23, 25 or 27 millimeters displaced as measured from center to center. Referring to FIG. 3, a view 300 of the appliance, including both upper and lower trays, illustrates line 320, as a measurement between retention hooks on one side of the trays.

Figure 4:
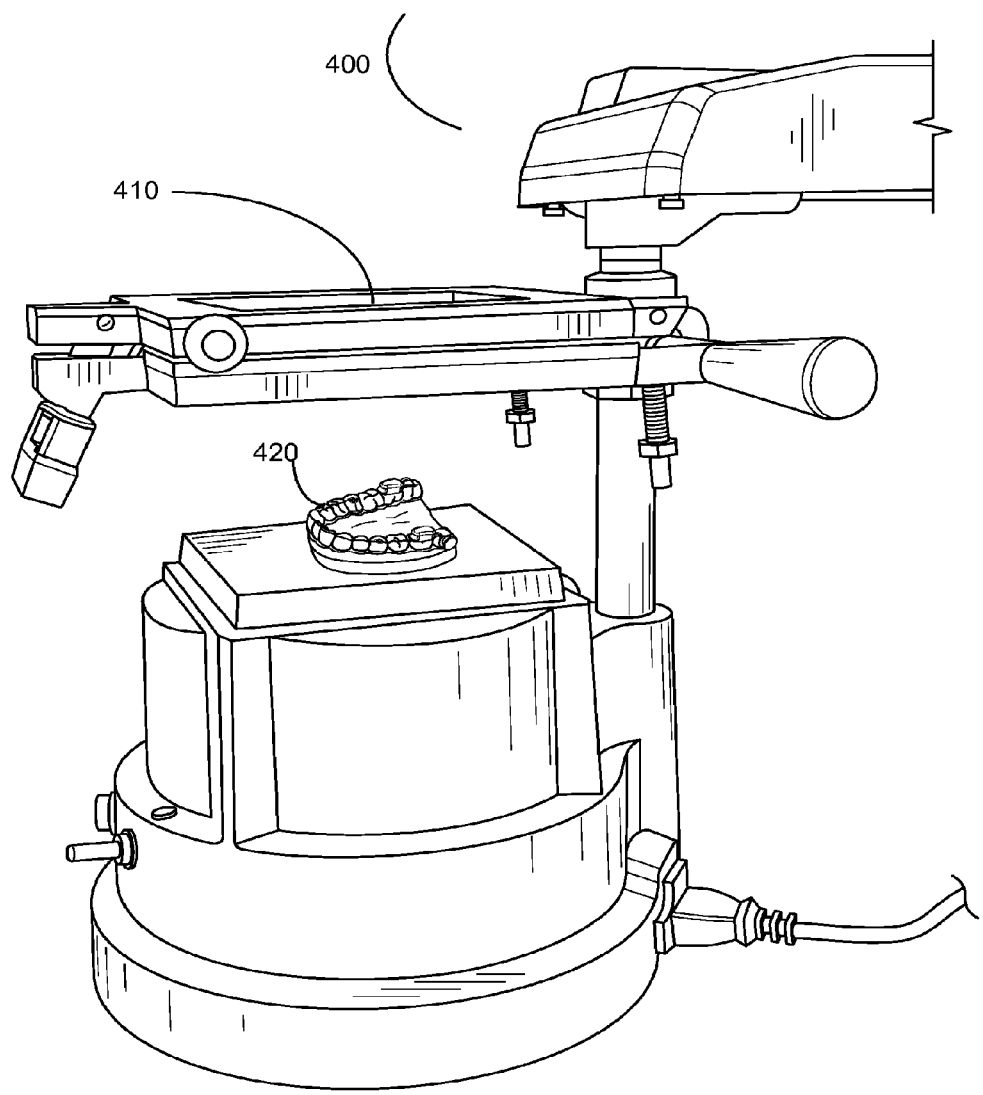
FIG. 4 illustrates a vacuum forming device forming plastic to a dental mold in accordance with an embodiment of the subject matter of the present application.

Next, in a machine typically seen in a dentist's office, such as a thermo-plastic machine 400 shown in FIG. 4. The dentist can place sheets of plastic 410 in the machine so that upon heating and applying a vacuum, the sheets are pulled down over the model 420 of the patent's upper and lower teeth, one at a time, with the temporarily attached first set of retention hooks and the set of bite pads integrated with the second set of retention hooks. The machine can operate on the upper and lower teeth models separately, as will be appreciated by those skilled in the art.

The heated plastic 410 encases, via vacuum sealing, each of the upper and lower teeth models and the retention hooks and bite pads to form upper and lower plastic trays adapted to fit over the teeth of the patient with the retention hooks and bite pads encased by the plastic.

In one embodiment, the bite pads can be placed to create an 8 mm anterior vertical opening between the upper and lower teeth to assist with treating sleep apnea. Information can be obtained from the patient as to any pressures on the teeth or gingiva.

Also, in an embodiment, the appliance, including both upper and lower trays, can be checked for comfort and evenness of opening from side to side with the patient. If pressures are felt by the patient on any tooth or any area of the gingiva, then these areas can be carefully relieved.

Some reasons for pressure on the teeth or gums include the following: (1) an inaccurate impression; and/or (2) a warped model. Advantageously, in a single office visit, there is generally no concern of intervening tooth movement or dental work since the impression can be obtained and the appliance manufactured on a same visit.

The machine 400 can be a thermo plastic machine, a vacuum-forming machine or the like. For example, the machine 400 can be configured to heat the sheets of plastic and vacuum seal the models of the upper and lower teeth to encase the temporarily attached first set of retention hooks, both right and left, and the set of bite pads integrated with the second set of retention hooks, both right and left as shown in FIG. 1.

After the plastic is vacuum sealed over the models, bite pads and retention hooks, the trays formed by the plastic are removed from the models. Removal can be accomplished by cutting with scissors, a dental burr, or a knife or other sharp implement.

Figure 5:
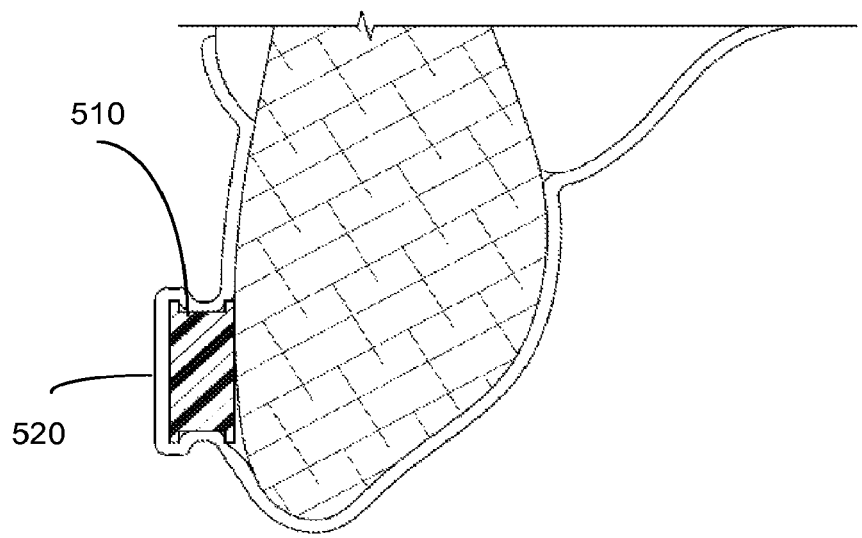
FIGS. 5 and 6 illustrate a retention hook encased in plastic as part of a dental appliance in accordance with an embodiment of the subject matter of the present application.

In an embodiment, the removal of the trays from the models causes the temporarily attached retention hooks and bite pads to be released from the models and become integrated with the plastic trays created by the vacuum sealing process. Referring to FIG. 5, to insure proper release from the models, in one embodiment, the retention hooks are formed such that each retention hook includes an edge 510 that enables the plastic 520 to seal around each retention hook to prevent the retention hooks from remaining attached to the respective model. In an embodiment, edge 510 can include a groove or other shape that enables the retention hooks to become secured by the plastic around the circumference of each retention hook to insure detaching of each retention hook from each model.

Figure 6:
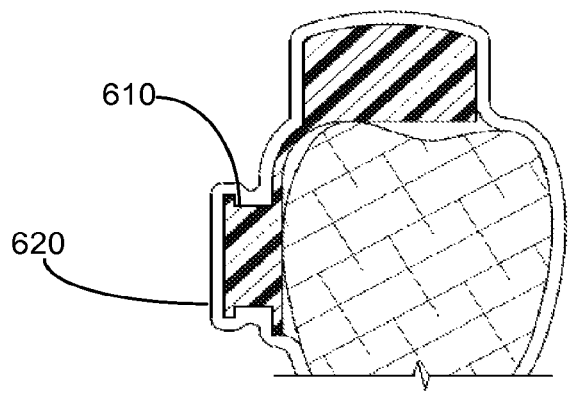

Likewise, referring to FIG. 6, retention hook includes an edge 610 to enable plastic 620 to encase the hook and bite pad combination to prevent the retention hook and bite pad combination from remaining attached to a model. Edge 610 can be a groove or other shape that insures detachment from the model. Likewise, each bite pad can be configured with a groove or the like to assist removing of the bite pad from the model.

Figure 7:
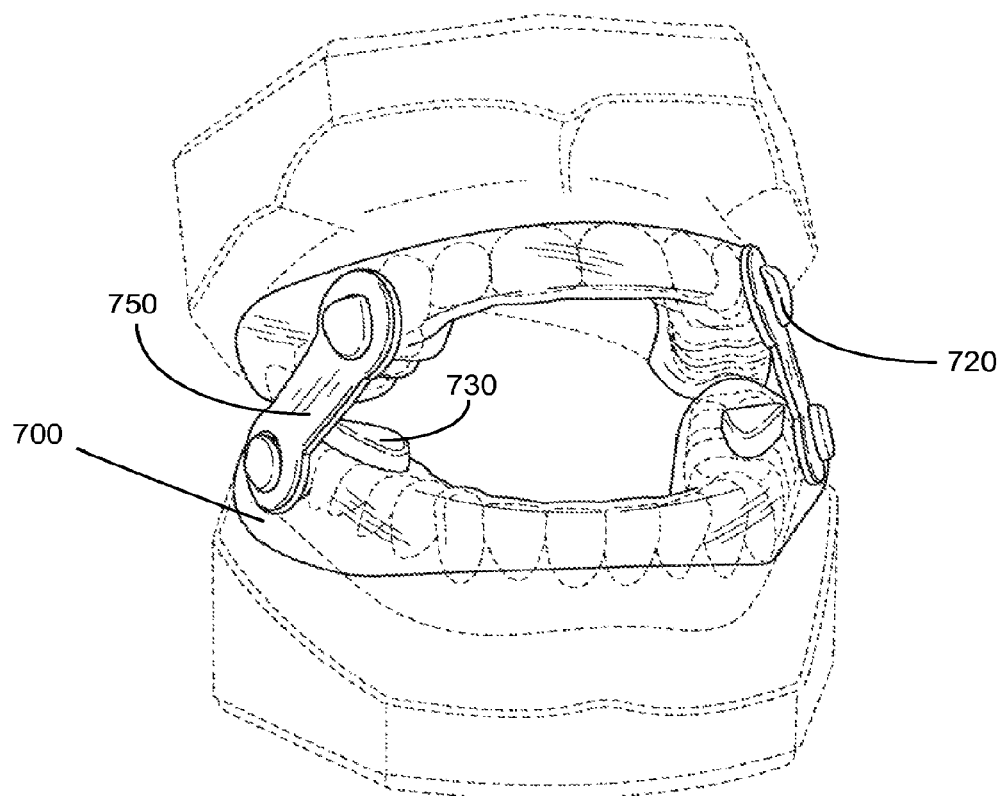
FIG. 7 illustrates a dental application in accordance with an embodiment of the subject matter of the present application.

Referring to FIG. 7, shown is an embodiment of the final appliance 700 including encased first set of retention hooks 720 and set of bite pads 730 integrated with the second set of retention hooks from the models to form a dental appliance 700 including both upper and lower trays.

FIG. 7 illustrates an embodiment including elastic bands 750 that couple the first tray and the second tray to enable the appliance 700 to treat sleep apnea. The vacuum forming over the retention hooks encases the retention hooks and the bite pads such that upon cooling, the appliance includes the retention hooks such that elastic bands 750 can be securely placed over the retention hooks during treatment.

The appliance 700 created with plastic covering the retention hooks and bite pads enables attachment of a pair of elastic bands 750 to be removably placed over the first and second sets of encased retention hooks to create a sleep apnea appliance, as shown in FIG. 7.

In one embodiment, the bite pads can be configured with one or more grooves and/or edges such that the plastic covering the retention hooks and bite pads does not prevent "snap on" bite pad extensions from being placed on each of bite pads. Thus, as shown in FIG. 7, bite pads 730 can include bite pad extensions that enable the bite pads to increase the vertical displacement between the upper and lower trays. In one embodiment, at least three different snap on bite pad extensions of various thicknesses can be configured to snap over the encased bite pads on the bottom tray to increase the amount of vertical displacement of the lower jaw when the appliance is worn.

Thus, if successful treatment for sleep apnea is not obtained with the vertical displacement rendered by the plastic-encased bite pads of the lower jaw, adequate vertical displacement can be obtained by temporarily snapping one of a plurality of thicknesses of "snap on bite pad extensions" over the encased bite pads.

In one embodiment, the choice of size of bite pad extension can be in accordance with a determined patient comfort including much air flow and efficacy.

In one embodiment, a bite pad extension can be permanently secured via a thin mix of orthodontic acrylic or a thin mix of light cure material. To permanently secure the bite pad extension, a prepared mix can be placed inside a dry "snap on bite pad extension". After firmly securing the extension over a dry encased bite pads right & left, mix material can escape through two holes in the bit pad extension to enable proper seating. The lower appliance with extensions on the bite pads can be cured as is known for acrylic material or cured with a light gun.

After bite pad extensions, if necessary, are attached over the encased bite pads to add vertical opening, a patient using the appliance can be fitted with a different appliance with known advancement and vertical opening for successful treatment via a permanent appliance.

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedical components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interactable and/or logically interacting components.

While certain features of the described implementations have been illustrated as disclosed herein, many modifications, substitutions, changes and equivalents will now occur to those skilled in the art. It is, therefore, to be understood that the appended claims are intended to cover all such modifications and changes as fall within the true spirit of the embodiments of the invention.

What is claimed is:

1. An oral appliance comprising:
   an upper tray adapted to fit tightly but removably over one or more occlusal surfaces of upper teeth of a patient, the upper tray including a first set of retention hooks encased by plastic of the upper tray; and
   a lower tray adapted to fit tightly but removable over one or more occlusal surfaces of teeth of the patient, the lower tray including a set of bite pads integrated with a second set of retention hooks, the second set of retention hooks and the set of bite pads encased by plastic of the lower tray, each bite pad of the set of bite pads having a bite surface which protrudes therefrom so as to engage one or more occlusal surfaces on the upper tray and thus maintain the one or more occlusal surfaces of the upper and lower trays in a predetermined spaced relation, when the upper and lower trays are fitted on the patient, wherein the set of bite pads integrated with a second set of retention hooks encased by plastic of the lower tray are adapted to enable one or more extensions to be attached to each bite pad of the set of bite pads.

2. The oral appliance of claim 1 further comprising: means to releasably attach an anterior and a posterior portion of each tray by placing a pair of elastic bands over the first set of retention hooks and the second set of retention hooks to enable a lower jaw of the patient to advance forwardly when the upper and lower trays are fitted over teeth of the patient.

3. The oral appliance of claim 2 wherein the pair of elastic bands is one of at least three different lengths of elastic bands and at least two different strengths.

4. The oral appliance of claim 1 wherein the one or more extensions include one of at least three thicknesses to increase an amount of vertical displacement of a lower jaw when the oral appliance is worn.

5. The oral appliance of claim 1 wherein the one or more extensions are permanently secured to each bite pad of the set of bite pads via one or more of a thin mix of orthodontic acrylic or a thin mix of light cure material.

* * * * *